(12) United States Patent
Schermer et al.

(10) Patent No.: US 7,031,528 B2
(45) Date of Patent: *Apr. 18, 2006

(54) INTERACTIVE SYSTEM FOR ANALYZING SCATTER PLOTS

(75) Inventors: Mack J. Schermer, Belmont, MA (US); Todd J. Stephan, Santa Clarita, CA (US)

(73) Assignee: PerkinElmer LAS, Inc., Boston, MA (US)

( * ) Notice: Subject to any disclaimer, the term of this patent is extended or adjusted under 35 U.S.C. 154(b) by 97 days.

This patent is subject to a terminal disclaimer.

(21) Appl. No.: 10/635,386

(22) Filed: Aug. 6, 2003

(65) Prior Publication Data

US 2004/0028277 A1    Feb. 12, 2004

Related U.S. Application Data

(63) Continuation of application No. 09/349,334, filed on Jul. 8, 1999, now Pat. No. 6,631,211.

(51) Int. Cl.
*G06K 9/62* (2006.01)

(52) U.S. Cl. .............................. 382/225; 378/6; 378/70; 704/245

(58) Field of Classification Search ................ 382/225; 378/6, 70; 704/245
See application file for complete search history.

(56) References Cited

U.S. PATENT DOCUMENTS

| | | | | | |
|---|---|---|---|---|---|
| 5,458,126 | A | * | 10/1995 | Cline et al. | 600/425 |
| 5,622,178 | A | * | 4/1997 | Gilham | 600/523 |
| 6,090,573 | A | * | 7/2000 | Laine et al. | 435/32 |
| 6,218,114 | B1 | * | 4/2001 | Peck et al. | 435/6 |
| 6,308,170 | B1 | * | 10/2001 | Balaban | 707/3 |
| 6,324,479 | B1 | * | 11/2001 | Friend et al. | 702/19 |
| 6,453,246 | B1 | * | 9/2002 | Agrafiotis et al. | 702/27 |
| 6,614,924 | B1 | * | 9/2003 | Aghajan | 382/149 |

* cited by examiner

*Primary Examiner*—Samir Ahmed
*Assistant Examiner*—Anand Bhatnagar
(74) *Attorney, Agent, or Firm*—Cesari and McKenna, LLP (57) ABSTRACT

A scanner system analyses data plotted in a scatter plot in accordance with user-specified criteria or statistical measures from the data population, to produce a scatter plot that displays in the plotted data the boundaries for the selection of out-lyer points and/or otherwise visually denotes in the plotted data which points are the out-lyer points. The scanner system analyzes the underlying data based on user-specified differential expression ratios, or based on criteria associated with the statistics of the data population, to produce out-lyer boundaries that are represented by diverging lines. Alternatively, the system may analyze the underlying data based on absolute expression levels, to produce boundaries that are represented in the plot by lines that meet at an identity line of slope 1. The scanner system may also combine several criteria and produce boundaries that denote as out-lyers the data that, for example, show both sufficient differential expression and also include individual expressions that are sufficiently above an associated noise floor.

14 Claims, 6 Drawing Sheets

INTERACTIVE SYSTEM FOR ANALYZING SCATTER PLOTS

CROSS-REFERENCE TO RELATED APPLICATION

The present application is a continuation of commonly assigned U.S. patent application Ser. No. 09/349,334, which was filed on Jul. 8, 1999 now U.S. Pat. No. 6,631,211, by Schermer et. al for an Interactive System for Analyzing Scatter Plots, and is hereby incorporated by reference.

BACKGROUND OF THE INVENTION

Microarray biochips are being increasingly used for the performance of large numbers of closely related chemical tests. For example, to ascertain the genetic differences between lung tumors and normal lung tissue one might deposit small samples of different DNA sequences on a microscope slide and chemically bond them to the glass. Ten thousand or more such samples can easily be arrayed as dots on a single microscope slide using mechanical microarraying techniques. Next, sample RNA is extracted from normal lung tissue (a control sample) and from a lung tumor (a test sample). The RNA represents all of the genes expressed in these tissues and the differences in the expression of RNA between the diseased tissue and the normal tissue can provide insights into the cause of the cancer and perhaps point to possible therapeutic agents as well. The "probe" samples from the two tissues are labeled with different fluorescent dyes. A predetermined amount of each of the two samples is then deposited on each of the microarray dots where they competitively react with the DNA molecules. The RNA molecules that correspond to the DNA strands in the microarray dots bind to the strands and those that do not are washed away.

The slide is subsequently processed in a scanner that illuminates each of the microarray dots with laser beams whose wavelengths correspond to the fluorescences of the labeling dyes. The fluorescent emissions are sensed and their intensity measured to ascertain, for each of the microarray dots, the degree to which the RNA samples correspond to the respective DNA sequences. In the experiment outlined above the image scanner separately senses the two fluorescences, and thereby provides for each dot two numerical values, or "expression levels," that represent reactions of the RNA extracted from the normal and diseased tissues. The scanner may then plot the data on a scatter plot, which has axes that correspond, respectively, to the intensity levels of the two fluorescences. A user then analyses the pattern of the data on the scatter plot.

The purpose of these experiments is to identify individual data points that are located sufficiently far from an identity line, i.e., a line in which the two intensities are the same, or some other closed-form mathematical function to denote a significant response difference. These points are commonly referred to as "out-lyers." In other types of experiments, the purpose is to determine whether the data produces a scatter plot pattern that approximates the identity line, some other straight line, or some other function, such as, for example, a parabola. In these experiments, the observer of the plot judges the closeness of the correlation between the plotted data points and the locus of the line produced by the mathematical function. The invention described below is concerned with the types of experiments in which out-lyers are identified.

The out-lyers that are of particular interest in the experiment described above correspond to genes that are sufficiently "differentially expressed." Differential gene expression is most often measured as the ratio of the control tissue expression level and the test tissue expression level, where an expression level is the absolute value of the associated fluorescence intensity.

Genes that are nearly equally expressed in both the control tissue and the test tissue will produce scatter plot data that are on or near the identity line, while genes that are differentially expressed will produce plot data that are farther from the identity line. Genes with low expression levels will produce plot data that are near the origin, or (0,0) point, regardless of their differential expression levels. The low expression levels expression can indicate lower data reliability, due to a low signal-to-noise value of that experiment. Accordingly, the experimenter may choose to omit the data from these genes from further study.

The identification of the genes that are candidates for further study is often done subjectively by visually judging which plotted points of the scatter plot are sufficiently far from the origin, that is, have high enough signal levels to justify confidence in the data, and/or are sufficiently far from the identity line, and thus, strongly differentially expressed. Known computer programs designed for the analysis of differential gene expression data often display a scatter plot, and provide to the user a mechanism to identify individual points of interest. For each identified point, the program may, for example, display or otherwise process the underlying gene data that generated the plotted point. Once the plotted points that meet the selection criteria have been identified by the user, the user may then collect or otherwise process the results for further analysis and experimentation.

It is simple to make qualitative judgements of the characteristics of individual plotted points in scatter plots that are comprised of a relatively small number of points. However, it is difficult to judge the differential expression ratio of the points, and/or to judge which points are just above or just below any particular expression level threshold. Further, these judgments and the identification of points of interest are more difficult to make with scatter plots that contain hundreds or thousands of data points. Accordingly, they are difficult for use with scatter plots associated with microarrays.

SUMMARY OF THE INVENTION

The inventive scanner system analyses data plotted in a scatter plot in accordance with user-specified criteria or statistical measures from the data population, to produce a scatter plot that displays in the plotted data the boundaries for the selection of out-lyer points and/or otherwise visually denotes in the plotted data which points are the out-lyer points. The scanner system may, for example, analyze the underlying data based on user-specified differential expression ratios, or based on criteria associated with the statistics of the data population, to produce out-lyer boundaries that are represented by diverging lines. Alternatively, the system may analyze the underlying data based on absolute expression levels, to produce boundaries that are represented in the plot by lines that meet at the identity line. The scanner system may also combine several criteria and produce boundaries that denote as out-lyers the data that, for example, show both sufficient differential expression and also include individual expressions that are sufficiently above an associated noise floor.

The scanner system also allows a user to inter-actively specify various selection criteria, for example, various differential expression ratios, and view the associated boundaries. The user can then determine which ratio is appropriate for the particular data. Alternatively, the user may specify desired numbers of out-lyer points, and have the system set the appropriate differential expression ratios for the data population. The system then produces plots that display the associated boundaries.

The system then "filters" the data based on the user and/or system specified selection criteria, and retains in a file for further study the underlying gene-specific information associated with the data points that are located outside of the boundaries.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
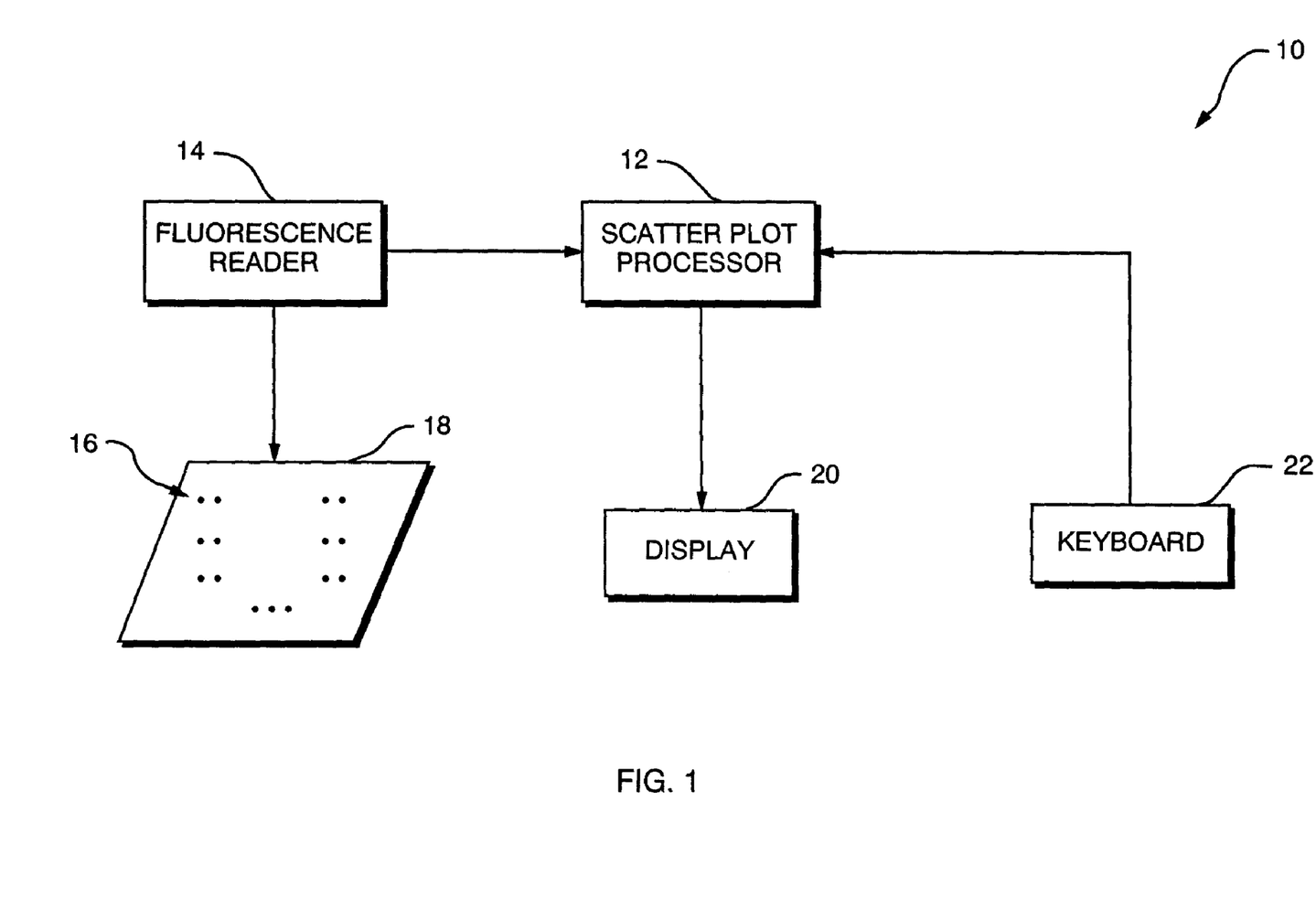
FIG. 1 is a functional block diagram of a system constructed in accordance with the invention.

Referring now to FIG. 1, a system 10 for analyzing scatter plot information includes a scatter plot processor 12 that receives information relating to fluorescent intensities from a fluorescence reader 14. The fluorescence reader 14 operates in a conventional manner to determine the different fluorescent intensities of dots 16 on a microarray 18. The microarray 18 generally includes thousands of target genes in the form of microarray dots 16 that, based on the genes present in control and test probe samples, respond appropriately to the fluorescent wavelengths associated, respectively, with the control and test tissue fluorescent dyes. For each dot, the fluorescent reader 14 provides to the scatter plot processor 12 both a control expression level and a test expression level.

The scatter plot processor 12 produces a scatter plot that includes a data point for each dot on the microarray, and a display unit 20, such as a computer monitor, displays the plot. As discussed in more detail below, the scatter plot processor also adds boundary lines to the scatter plot, to denote that certain data points are out-lyers, and thus, candidates for further study. A user may interactively set the boundary conditions by specifying selection criteria through a keyboard 22 or other data input device. Also, the user may inter-actively change the selection criteria, and the system then draws new boundaries. The user can thus modify the selection criteria to fit the data population.

Figure 2:
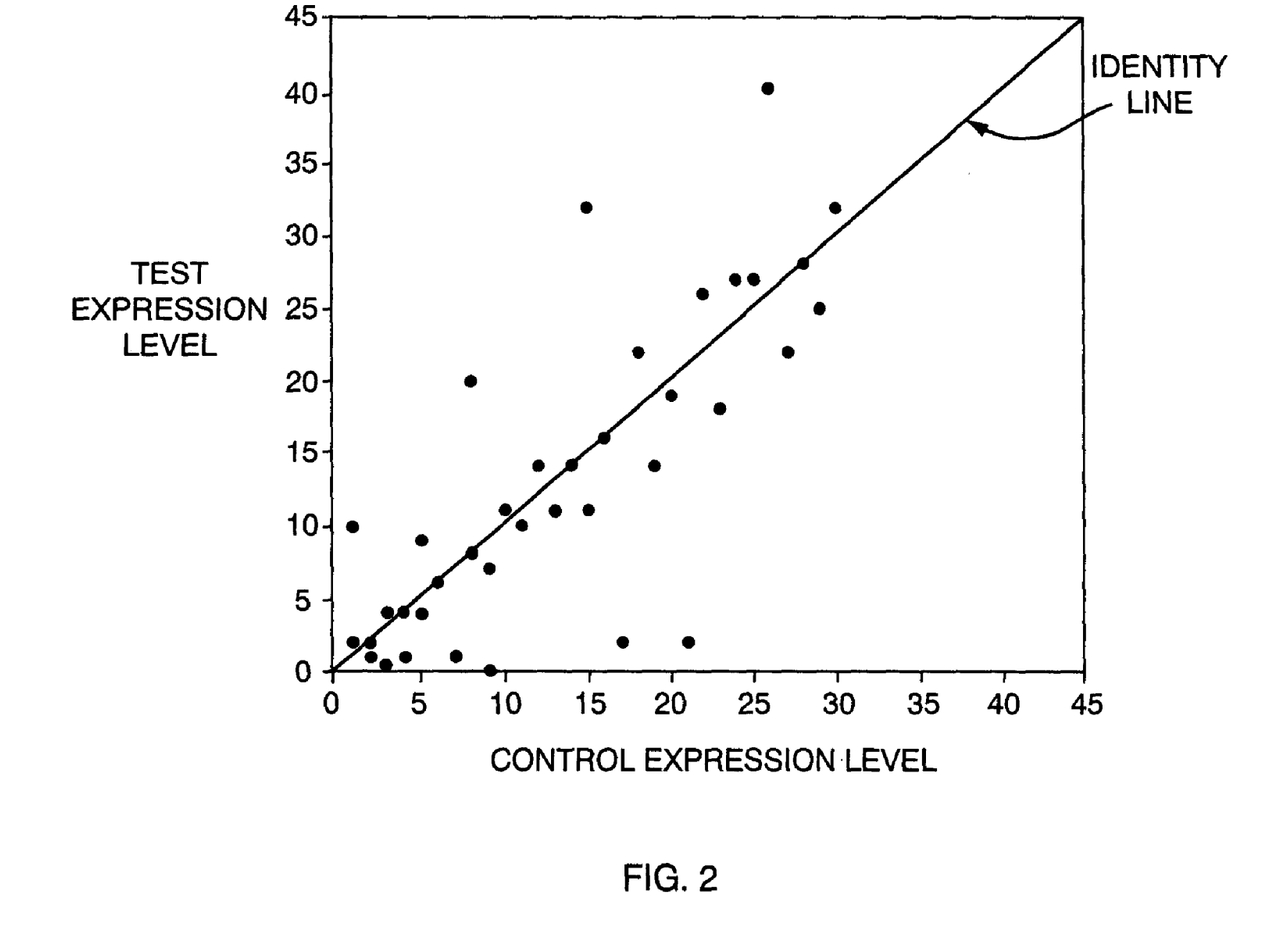
FIG. 2 is a drawing of a scatter plot produced by the system.

For ease of understanding, we include drawings that depict relatively small numbers of data points. In use, the system produces scatter plots with hundreds or thousands of data points. Referring now to FIG. 2 a scatter plot is shown before the boundary lines are supplied. The scatter plot includes an identity line that denotes equal expressions for both types of fluorescence. The data points on the identity line thus represent genes that are similarly expressed in the control tissue and the test tissue, and are of little interest for further study. Conversely, the points that are some distance away from the identity line represent genes that differ between the control sample and the test sample.

The genes that are sufficiently differentially expressed are of interest for further study to determine, for example, how the healthy tissue differs from the diseased tissue.

Figure 3:
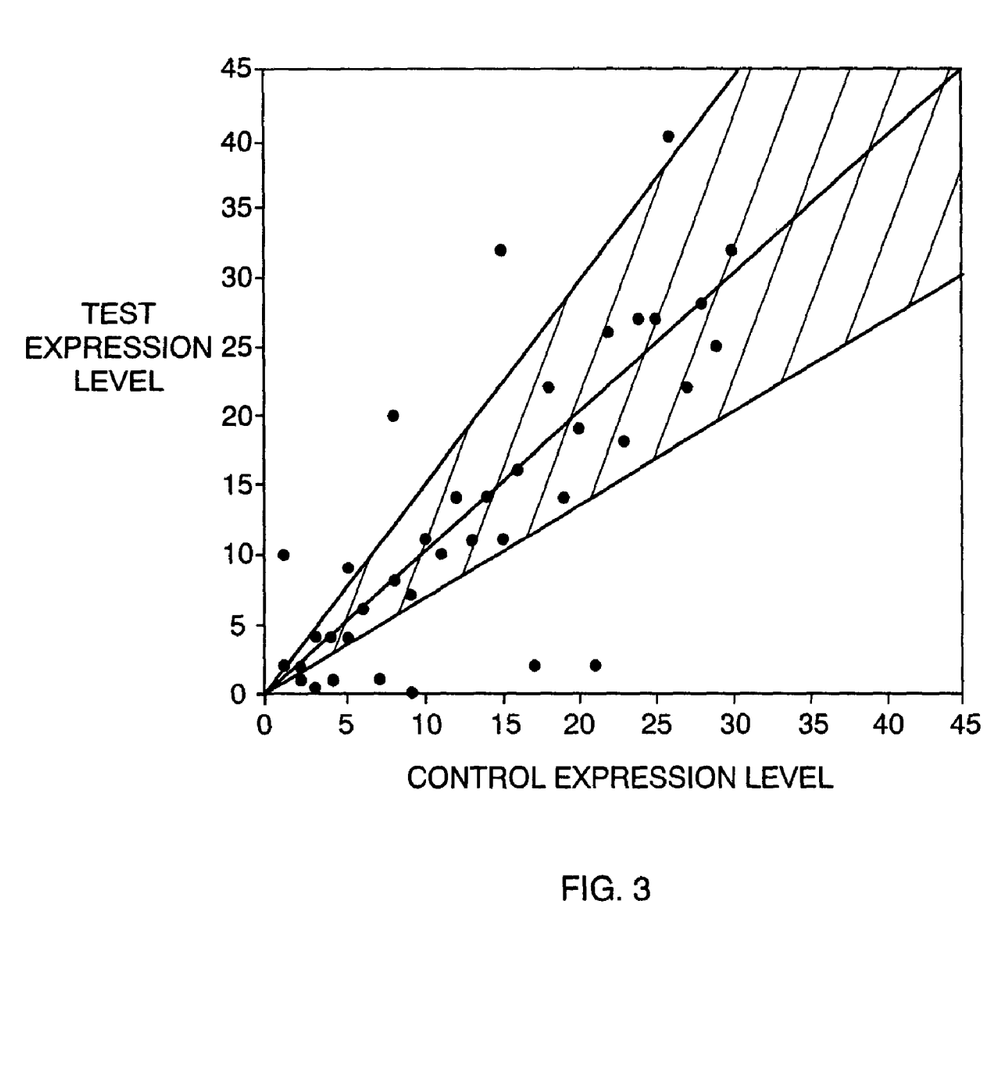
FIGS. 3–6 are drawings of scatter plots containing boundary lines.

A user may specify the selection criteria that distinguish out-lyer points from other points as, for example, a particular ratio of test expression level to control expression level, that is, as a differential expression ratio. As shown in FIG. 3, the associated boundary lines 20 and 22 start close to the origin and diverge, with each boundary line having a slope that is associated with the specified differential expression ratio. The drawing depicts boundaries associated with a differential expression ratio of 1.5. The boundary line 20 has a slope of 1.5 and the boundary line 22 has a slope of $1/1.5$ or 0.66. The data points that lie between the two boundary lines are deemed to be sufficiently close to the identity line, based on the user-specified criteria, to be of little interest for further study. The points that lie outside of the boundary lines meet the user-specified criteria for out-lyers. As shown in the drawing, the system may include cross-hatching to further distinguish the non-selected points in the plot. Alternatively, the system may dim the points inside the boundaries, change their color or similarly change their visual properties with respect to the point outside the boundaries.

To determine if the boundary criteria are appropriate, a user may look at one or more of the data points in more detail. The user thus selects the point or points of interest, and the scatter plot processor 12 displays some or all of the underlying gene information for the points. The user may then determine that the boundary lines should be redrawn to include or exclude certain points for further study. The user next specifies a different ratio, as appropriate.

Further, as discussed above, the scatter plot processor 12 filters the data based on the boundaries, and stores in a data file the underlying gene-specific information for each of the out-lyer points. The user may then study or analyze this information.

After viewing the results, a user may wish to specify selection criteria based on the data population. For example, the user may specify that the out-lyer points must be more than one standard deviation from the identity line. The scatter plot processor will then analyze the data population and depict the applicable boundaries in the scatter plot display. A user may next, as discussed above, select individual data points and review the underlying data to determine if the selection criteria is appropriate. At the same time, the scatter plot processor filters the data and preserves in a data file the underlying gene information relating to the out-lyer points as defined by the new boundaries.

Figure 4:
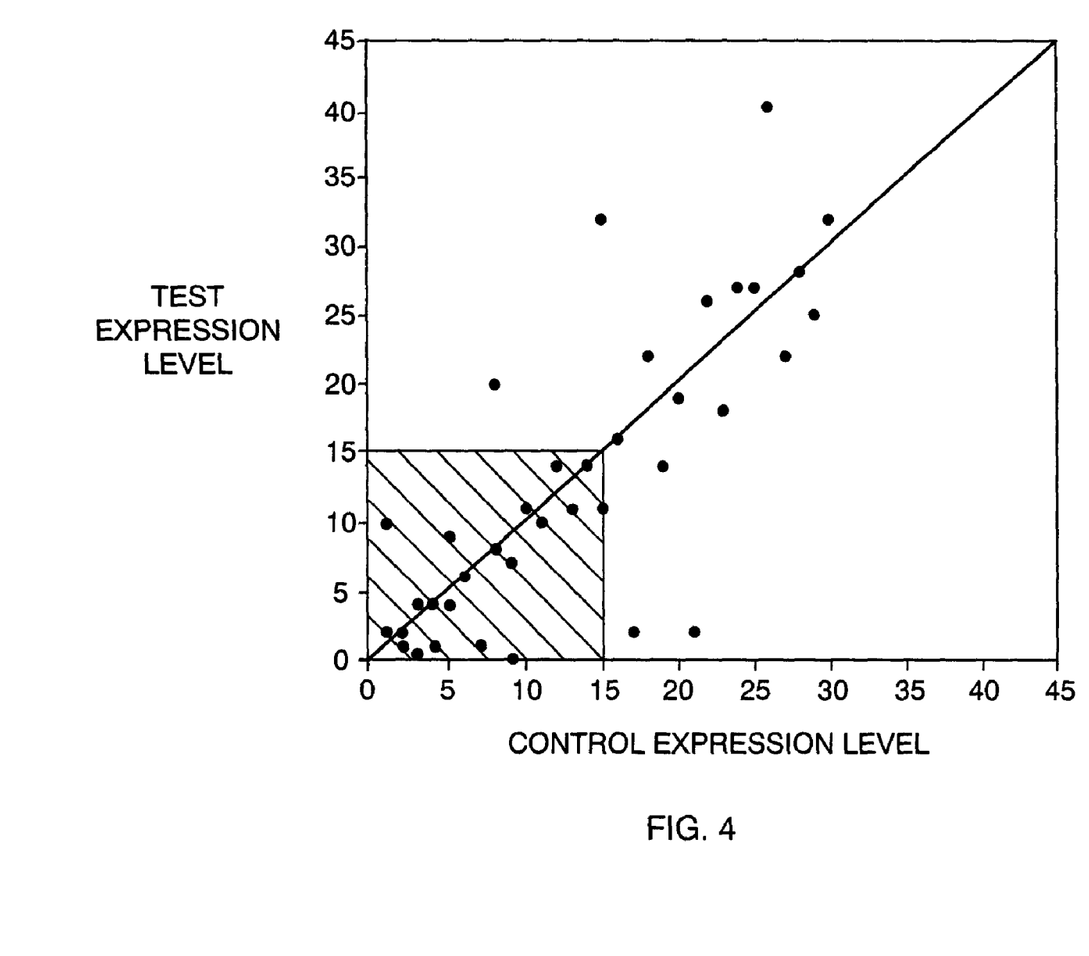

Referring now to FIG. 4, the user may base the selection criteria on the individual expression levels. The points nearest the origin, whether they are inside or outside of the differential expression boundaries, represent data in which the fluorescence intensities indicate relatively low response to the test or control samples. Indeed, some of these points may be within the noise level of the system. Accordingly, a user may specify a particular noise floor, and the scatter plot processor will then define and depict noise boundaries that set a minimum expression level for the out-lyer points. As depicted in FIG. 4, the noise boundaries 40 and 42 represent expression levels of 15. The out-lyer points thus have at least one of the control and test expression levels above 15. The selection criteria for the noise floor may instead be a particular percentage of the data points, and the system then sets the noise boundaries based on the data population.

Figure 5:
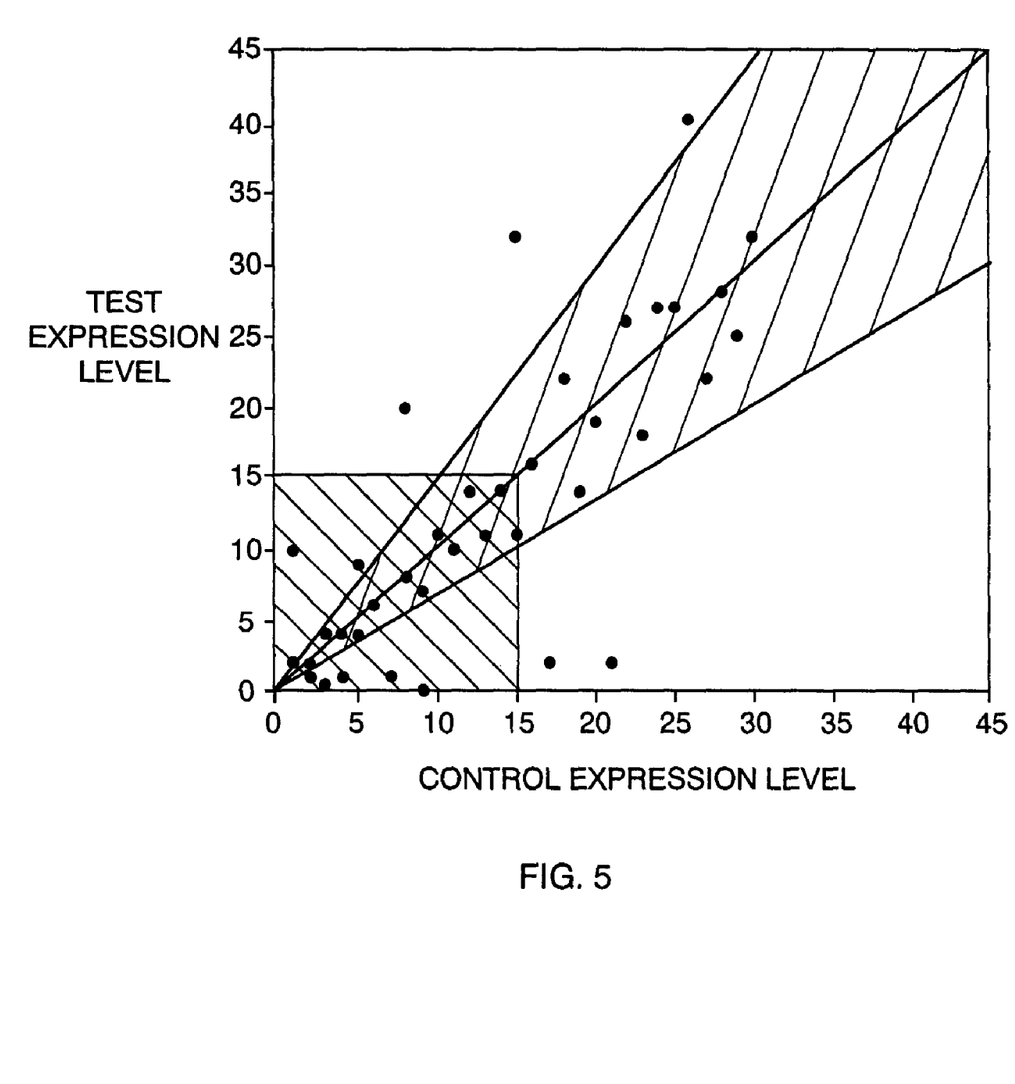

As shown in FIG. 5, the system may depict both noise boundaries and differential expression ratio boundaries on the same scatter plot. The out-lyer points are then the points that are outside both sets of boundaries.

The selection criteria for the noise floor may instead be a particular percentage of the data points. The system then sets the noise boundaries based on the data population.

Figure 6:
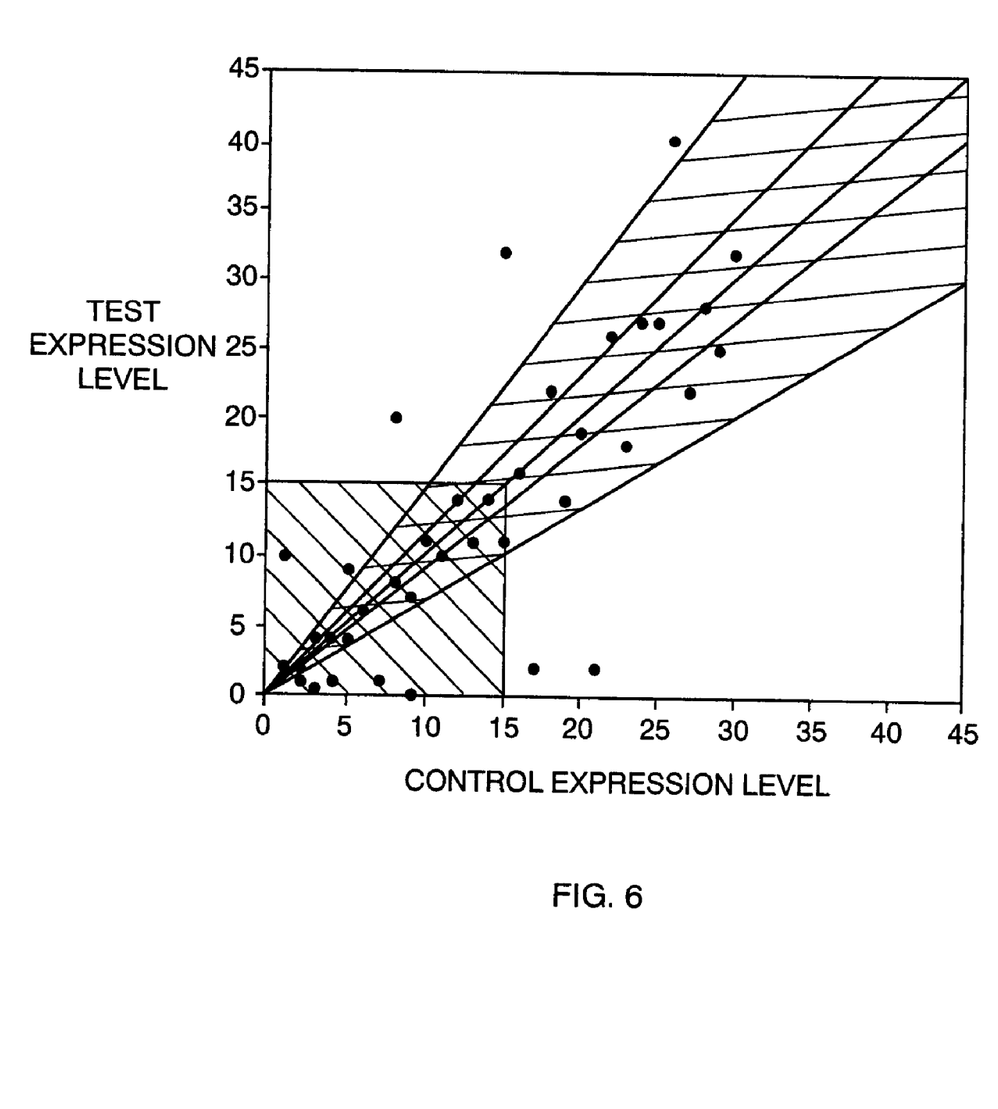

As shown in FIG. 6, a user may specify a plurality of boundary conditions, such that the scatter plot includes multiple sets of boundary lines that represent, for example, several differential expression levels. The scatter plot processor can then filter the data with respect to each of the various boundary conditions, and set up a plurality of data files that contain information relating to out-lyers as defined by the boundaries of interest. Alternatively, the scatter plot processor can filter the data based on particular, selected boundary lines.

The user may instead specify the selection criteria as a particular number of out-lyer points. For example, the user may specify that it wishes to see the boundary conditions that define five points as out-lyers. The scatter plot processor then determines an applicable differential expression ratio that satisfies the user's criteria, and displays the scatter plot with lines denoting the applicable boundaries. The system may also include the applicable differential expression ratio in the display. Again, the user may specify different selection criteria, to re-position the boundary lines or to superimpose additional boundary lines on the display. The scatter plot processor may then save information relating to the various boundary conditions and the underlying data for each of the out-lyer points in associated data files.

We have discussed the scatter plot system in terms of analyzing differential gene expression. However, the system may be used to analyze any type of scatter plot and designate the out-lyer points in the scatter plot. We have discussed including boundary lines in the scatter plot as a way of visually distinguishing out-lyer points from the other data points. The out-lyer plot points may instead be distinguished by plotting them in colors that differ from the colors of the non-selected plot points, by depicting the background beyond the boundaries in different colors, and so forth. Further, the system may produce the scatter plot with X and Y axes that have logarithmic scales or axes that have different scales from one another. The scales may be specified by the user, or the system may set them based on the data population.

The invention claimed is:

1. A method for analyzing data, the method comprising:
   producing and displaying a scatter plot that contains a plotted point for each of the data;
   determining the locations of various sets of one or more boundaries that segment the scatter plot into pluralities of regions that correspond to selection criteria interactively supplied by a user, with one or more of the sets defining at least one region of interest;
   recording information related to the data whose plotted points are located in a given region of interest;
   selecting one or more plotted points in the given region of interest; and
   retrieving and displaying the recorded information corresponding to the one or more selected plotted points.

2. The method of claim 1, wherein the recorded information related to the data whose plotted points are located in the given region of interest is gene information.

3. The method of claim 1, wherein the recorded information related to the data whose plotted points are located in the given region of interest is stored in a computer file or data base.

4. The method of claim 3, wherein the recorded information corresponding to the one or more selected plotted points is retrieved from the computer file or data base.

5. The method of claim 1, wherein at least one boundary in the sets of one or more boundaries is derived based on one of the following:
   (i) a specified differential expression ratio calculated as the quotient of a variable associated with an x-axis and a variable associated with a y-axis, or
   (ii) a predetermined noise level, or
   (iii) statistics of the data, or
   (iv) a predetermined number of points are located outside the boundary.

6. A microarray scanning system adapted to acquire fluorescence measurements representative of the extent to which a genetic sample reacts with both a test sample and a control sample, the microarray scanning system comprising:
   a fluorescence reader that generates a pair of test-sample and control-sample fluorescence measurements for each of a plurality of genetic samples;
   a processor that receives the pairs of test-sample and control-sample fluorescence measurements generated by the fluorescence reader and produces a scatter plot graphing each test-sample fluorescence measurement against its corresponding control-sample fluorescence measurement;
   a data input device that interactively receives selection criteria from a user and forwards the user-specified selection criteria to the processor, wherein the processor is configured to process the user-specified selection criteria to determine locations of various sets of one or more boundaries in the scatter plot; and
   a display unit that displays the scatter plot and superimposes the sets of one or more boundaries over the displayed scatter plot.

7. A method for displaying data on a display unit, the method comprising:
   plotting the data as pairs of x-coordinates and y-coordinates in an orthogonal coordinate system to generate a scatter plot that is displayed on the display unit;
   determining the location of a first set of one or more boundaries in the orthogonal coordinate system based on a first set of selection criteria interactively provided by a user, with at least one boundary in the first set of one or more boundaries defining a first region of interest in the orthogonal coordinate system;
   superimposing the first set of one or more boundaries over the scatter plot displayed on the display unit;
   changing the visual properties of pairs of x-coordinates and y-coordinates displayed by the display unit in the first region of interest;
   determining the location of a second set of one or more boundaries in the orthogonal coordinate system based on a second set of selection criteria interactively provided by a user, with at least one boundary in the second set of one or more boundaries defining a second region of interest in the orthogonal coordinate system;
   removing the first set of one or more boundaries from the scatter plot displayed on the display unit and returning the visual properties of pairs of x-coordinates and y-coordinates in the first region of interest to their original visual properties;
   superimposing the second set of one or more boundaries over the scatter plot displayed by the display unit; and
   changing the visual properties of pairs of x-coordinates and y-coordinates displayed by the display unit in the second region of interest.

8. The method of claim 7, wherein the first and second regions of interest are the same region displayed on the display unit.

9. The method of claim 7, wherein pairs of x-coordinates and y-coordinates located in the first and second regions of interest are displayed by the display unit using a different color than pairs of x-coordinates and y-coordinates located outside the respective first and second regions of interest.

10. The method of claim 7, wherein pairs of x-coordinates and y-coordinates located in the first and second regions of interest are displayed by the display unit using a different intensity than pairs of x-coordinates and y-coordinates located outside the respective first and second regions of interest.

11. The method of claim 7, wherein pairs of x-coordinates and y-coordinates located in the first and second regions of interest are displayed by the display unit using a different background color than pairs of x-coordinates and y-coordinates located outside the respective first and second regions of interest.

12. A display device adapted to display data, the display device comprising:

means for plotting the data as pairs of x-coordinates and y-coordinates in an orthogonal coordinate system to generate a scatter plot that is displayed on the display unit;

means for determining the location of a first set of one or more boundaries in the orthogonal coordinate system based on a first set of selection criteria interactively provided by a user, with at least one boundary in the first set of one or more boundaries defining a first region of interest in the orthogonal coordinate system;

means for superimposing the first set of one or more boundaries over the scatter plot displayed on the display device;

means for changing the visual properties of pairs of x-coordinates and y-coordinates displayed by the display device in the first region of interest;

means for determining the location of a second set of one or more boundaries in the orthogonal coordinate system based on a second set of selection criteria interactively provided by a user, with at least one boundary in the second set of one or more boundaries defining a second region of interest in the orthogonal coordinate system;

means for removing the first set of one or more boundaries from the scatter plot displayed on the display device and returning the visual properties of pairs of x-coordinates and y-coordinates in the first region of interest to their original visual properties;

means for superimposing the second set of one or more boundaries over the scatter plot displayed by the display device; and means for changing the visual properties of pairs of x-coordinates and y-coordinates displayed by the display device in the second region of interest.

13. A computer-readable medium having instructions for execution on a processor, said instructions for a method for analyzing data, the method comprising:

producing and displaying a scatter plot that contains a plotted point for each of the data;

determining the locations of various sets of one or more boundaries that segment the scatter plot into pluralities of regions that correspond to user specified selection criteria, with one or more sets including at least one region of interest;

recording information related to the data whose plotted points are located in a given region of interest;

selecting one or more plotted points in the given region of interest; and retrieving and displaying the recorded information corresponding to the one or more selected plotted points.

14. The computer-readable medium of claim 13 wherein said instructions further include, in the step of recording information, storing the information in a data file or database.

* * * * *